United States Patent [19]

Nedez et al.

[11] Patent Number: 5,756,791
[45] Date of Patent: May 26, 1998

[54] PROCESS FOR THE ADSORPTION OF CHELATED ORGANOMETALLIC COMPOUNDS AND ALUMINA BEADS INCLUDING A CHELATED ORGANOMETALLIC COMPOUND

[75] Inventors: Christophe Nedez, Asnieres sur Seine; Bernard Taxil, Salindres, both of France

[73] Assignee: Rhone-Poulenc Chimie, Courbevoie Cedex, France

[21] Appl. No.: 630,123

[22] Filed: Apr. 10, 1996

[30] Foreign Application Priority Data

Apr. 10, 1995 [FR] France .................................. 95 04259

[51] Int. Cl.$^6$ ................................ C07F 9/00; C07F 7/00
[52] U.S. Cl. ............................ 556/42; 556/54; 556/113; 556/177; 502/162; 526/160
[58] Field of Search ........................ 556/42, 54, 113, 556/177; 502/162; 526/160

[56] References Cited

FOREIGN PATENT DOCUMENTS

| 0067708 | 12/1982 | European Pat. Off. . |
| 0379394 | 7/1990 | European Pat. Off. . |
| 0073525 | 1/1961 | France . |
| 1383076 | 4/1965 | France . |
| 3029802 | 3/1981 | Germany . |

*Primary Examiner*—Porfirio Nazario-Gonzalez
*Attorney, Agent, or Firm*—Burns, Doane, Swecker & Mathis, L.L.P.

[57] ABSTRACT

The invention relates to a process for the adsorption of chelated organometallic compounds, in which the said compounds are placed in contact with alumina-based beads produced by forming by agglomeration of an alumina powder using a rotational technique and exhibiting a volume of pores of diameter greater than 100 Å of at least 0.10 cm$^3$/g, a volume of pores of diameter greater than 1 μm of at least 0.05 cm$^3$/g and a diameter of not more than 4 mm. It also relates to alumina beads including a chelated organometallic compound.

10 Claims, No Drawings

5,756,791

PROCESS FOR THE ADSORPTION OF CHELATED ORGANOMETALLIC COMPOUNDS AND ALUMINA BEADS INCLUDING A CHELATED ORGANOMETALLIC COMPOUND

The invention relates to a process for the adsorption of chelated organometallic compounds, in which the said compounds are placed in contact with alumina-based beads of appropriate characteristics. It relates more particularly to a process for the purification of polyolefins obtained by polymerization of olefins in the presence of coordination catalysts. It also relates to alumina beads including a chelated organometallic compound.

Polyolefins are generally prepared by polymerization of monomers with possible addition of comonomers such as 1-butene, 1-octene, etc, in the presence of polymerization catalysts including elements of groups IVB, VB and VIB of the Periodic Classification of the elements, and more particularly vanadium, titanium and zirconium. These catalysts also include, as reducing agents for the organometallic compounds (metal alkyl), metal hydrides or metal hydroxides. These catalysts, generally called transition catalysts, exhibit a high catalytic activity for the polymerization of olefins.

However, once the polymerization is finished, the polyolefins obtained are found to be contaminated with metal residues originating from the catalysts and it is therefore indispensable to purify them before they are employed, to avoid any toxicity like an interfering coloration or degradation.

Furthermore, processes for the polymerization of olefins generally include a stage of recovery of the monomers which have not reacted during the polymerization and of the solvents present in the polyolefins, these solvents and monomers being recycled into the polymerization unit. The presence of metals in these compounds gives rise to plant corrosion problems.

One process for removing the metal residues originating from the catalysts consists in placing the mixture originating from the polymerization in contact with organic compounds. As a result, a reaction of complex formation between the metal residues and the organic compounds introduced is produced, resulting in chelated organometallic compounds.

Next, in order to separate these chelated organometallic compounds from the polyolefins, it is known to employ various adsorbents, especially aluminas.

Among the adsorbents employed it is advantageous to employ adsorbents in the form of beads which can be handled more easily than powder or blocks of various shapes. In fact, a product in bead form can be conveyed using, for example, pneumatic systems, both for charging and discharging the purification columns.

Among the adsorbents, alumina can be easily formed into beads.

An objective of the present invention is to propose alumina beads for the adsorption of the chelated organometallic compounds, exhibiting a degree of adsorption which is improved in relation to those of the products of the prior art.

To this end, the invention relates to a process for the adsorption of chelated organometallic compounds, in which the said compounds are placed in contact with alumina-based beads produced by forming by agglomeration of an alumina powder using a rotational technique and exhibiting a volume of pores of diameter greater than 100 Å of at least 0.10 cm$^3$/g, a volume of pores of diameter greater than 1 μm of at least 0.05 cm$^3$/g and a diameter of not more than 4 mm.

The invention also relates to alumina beads including a chelated organometallic compound which are obtained after the placing in contact according to the process defined above.

The invention relates first of all to a process for the adsorption of chelated organometallic compounds, in which the said compounds are placed in contact with alumina-based beads produced by forming by agglomeration of an alumina powder using a rotational technique and exhibiting a volume of pores of diameter greater than 100 Å of at least 0.10 cm$^3$/g, a volume of pores of diameter greater than 1 μm of at least 0.05 cm$^3$/g and a diameter of not more than 4 mm.

The process preferably uses beads exhibiting a volume of pores of diameter greater than 100 Å greater than 0.15 cm$^3$/g and a volume of pores of diameter greater than 1 μm greater than 0.08 cm$^3$/g.

Still more preferably, the beads exhibit a volume of pores of diameter greater than 100 Å greater than 0.2 cm$^3$/g and a volume of pores of diameter greater than 1 μm greater than 0.1 cm$^3$/g.

The volume of pores of diameter greater than 100 Å, or than 1 μm, represents the cumulative volume created by all the pores of size greater than a diameter of 100 Å, or than 1 μm. These volumes are measured by the mercury penetration technique, in which Kelvin's law is applied.

According to the process of the invention the beads may advantageously exhibit a diameter smaller than 3 mm, preferably smaller than 2.5 mm. The diameters of the beads are measured by means of a sliding calliper gauge.

The processes for preparing beads that can be employed in the process according to the invention are known to a person skilled in the art.

For example, one process for the preparation of these beads exhibiting a controlled porosity and diameter may consist in forming alumina beads by agglomeration of an alumina powder. Following this agglomeration the beads obtained may be subjected to various operations intended to improve their mechanical strength, such as maturing by being kept in an atmosphere of controlled moisture content, followed by calcination and then by impregnation of the beads with a solution of one or more acids and a hydrothermal treatment in a confined atmosphere. Finally, the beads are dried and calcined so as to be activated. For example, the beads may be calcined at a temperature comprised between 300° and 1000° C., preferably between 300° and 800° C.

This type of process makes it possible to obtain beads of controlled pore sizes and distributions, these sizes and these distributions being generally produced during the agglomeration stage.

The porosity may be produced by various means, like the choice of the particle size of the alumina powder or the agglomeration of a number of alumina powders of different particle sizes. Another method consists in mixing with the alumina powder, before or during the agglomeration stage, a compound called a pore-former, which disappears completely on heating and thus produces a porosity in the beads.

Pore-forming compounds employed which may be mentioned, by way of example, are wood flour, charcoal, sulphur, tars, plastics or plastic emulsions such as polyvinyl chloride, polyvinyl alcohols, naphthalene or the like. The quantity of pore-forming compounds which are added is not critical and is determined by the desired pore volume.

The alumina powder employed as starting material can be obtained by conventional processes such as the precipitation or gel process and the process using rapid dehydration of an alumina hydroxide such as the Bayer hydrate (hydrargillite). The latter alumina is that preferred in the invention.

The agglomeration of the beads according to the invention is performed directly on the alumina powder using a rotational technique. A rotational technique is intended to mean any apparatus in which the agglomeration is performed by placing the product to be granulated in contact with itself and rotating it about itself. The rotary coating pan and the rotary drum may be mentioned as apparatus of this type.

The control of the volumes of the pores of a given diameter may also be carried out during this agglomeration stage by an appropriate adjustment of the rate of introduction of the alumina powder and optionally of water, of the speed of rotation of the apparatus or when a forming initiator is introduced.

The beads employed in the process according to the invention advantageously exhibit a specific surface of at least 100 m$^2$/g, preferably greater than 150 m$^2$/g, still more preferably greater than 200 m$^2$/g. This specific surface is a BET surface. A BET surface is intended to mean the specific surface determined by nitrogen adsorption in accordance with ASTM standard D 3663-78, established from the Brunauer-Emmett-Teller method described in the periodical "Journal of the American Chemical Society", 60, 309 (1938).

The process according to the invention makes it possible to obtain improved degrees of adsorption of the chelated organometallic compounds, which may reach more than 60%, the latter degree representing the ratio of metal adsorbed by the beads in relation to the initial quantity of metal introduced into the reaction mixture and in the conditions defined in the adsorption test below.

The beads may preferably include at least one compound of an element chosen from the group including the alkali and alkaline-earth metals. This compound of the element may be an oxide, a hydroxide, a salt of the element or a mixture of these. Examples which may be mentioned, in addition to hydroxides, are the sulphates, nitrates, halides, acetates, formates, carbonates and, more generally, the salts of, for example, carboxylic acids.

Elements chosen from sodium, potassium and calcium are preferably employed.

The content of the compound of the element chosen from the group of the alkali and alkaline-earth metals may be between 15 mmol and 150 mmol per 100 g of alumina, preferably between 15 and 100 mmol per 100 g of alumina.

The incorporation of these elements may be performed according to the teaching of Patent Application EP-A-0 379 394.

The present invention relates more particularly to the process making use of the beads described above for the adsorption of any chelated organometallic compound, more particularly based on metals chosen from those of the groups IVB, VB, VIB, VIIB, VIII, IB, IIB and, still more particularly, those based on vanadium, titanium, zirconium or copper.

The process according to the invention is especially suitable for the adsorption of any organometallic compound which has been chelated using organic compounds such as acetylacetone, 2-ethyl-1,3-hexanediol and di-2-ethylhexyl phosphate.

As a result, the process according to the invention can be suitable for the purification of polyolefins obtained by polymerization of olefins in the presence of a coordination catalyst system. The purification process may be of the type described above in the introduction to the present description and in which the beads are placed in contact with the mixture resulting from the polymerization, previously placed in contact with organic compounds.

The invention also relates to alumina beads including a chelated organometallic compound, the said beads being obtained after the placing of organometallic compounds in contact, according to the process of the invention, with alumina beads produced by forming by agglomeration of an alumina powder using a rotational technique and exhibiting a volume of pores of diameter greater than 100 Å of at least 0.10 cm$^3$/g, a volume of pores of diameter greater than 1 μm of at least 0.05 cm$^3$/g and a diameter of not more than 4 mm.

In the process according to the invention the said alumina beads are placed in contact with the organometallic compounds and adsorb them. At the end of the process of adsorption of the organometallic compounds the beads are removed from the reactor and alumina beads are obtained which are produced by forming by agglomeration of an alumina powder by a rotational technique, exhibiting a volume of pores of diameter greater than 100 Å of at least 0.10 cm$^3$/g, a volume of pores of diameter greater than 1 μm of at least 0.05 cm$^3$/g and a diameter of not more than 4 mm, on which the organometallic compounds are adsorbed.

These beads may be employed directly as supported metal catalysts in any type of catalysis using precious metals which is adapted to the nature of the adsorbed metal.

The following examples illustrate the invention without, however, limiting its scope.

EXAMPLES

Adsorption test

The adsorption tests were conducted on alumina beads preactivated at 300° C. for 2 h in order to remove any trace of moisture following their storage and in order to enable their effectiveness to be compared in identical conditions.

The beads are introduced into a beaker containing vanadium chelated with acetylacetone (VO(acac)$_2$) present in 200 ml of toluene in a concentration of 0.1% (by weight relative to the volume of toluene). They are left, with stirring, in contact with the compound for 48 h at 25° C. protected from air. The degree of adsorption of the vanadium chelated with acetylacetone by the alumina is checked by change in the concentration of the solution, measured by UV-visible spectroscopy.

All the beads tested in the examples were formed using a rotary coating pan and hydrargillite alumina.

Example 1

Influence of the volumes of the pores of diameter greater than 100 Å and 1 μm

|  | Diameter (mm) | Specific surface (m$^2$/g) | V$_{100 Å}$ (cm$^3$/g) | V$_{1 μm}$ (cm$^3$/g) | Degree of adsorption |
|---|---|---|---|---|---|
| Beads 1 comparative | 2.2 | 324 | 0.06 | 0.04 | 55.4% |
| Beads 2 | 1.9 | 344 | 0.17 | 0.09 | 64% |
| Beads 3 | 1.9 | 333 | 0.26 | 0.15 | 71.5% |
| Beads 4 | 1.9 | 350 | 0.27 | 0.20 | 81.2% |
| Beads 5 | 1.9 | 308 | 0.30 | 0.23 | 78.6% |

It is found that the degree of adsorption of beads 1, exhibiting a volume of pores of diameter greater than 100 Å of 0.06 cm$^3$/g and a volume of pores of diameter greater than 1 μm of 0.04 cm$^3$/g is 55.4%, whereas the degree of adsorption of the beads 2 to 5, which conform to the characteristics of the beads according to the invention, is greater than 64%.

Example 2

Influence of the bead diameter

|  | Diameter (mm) | Specific surface (m²/g) | $V_{100 Å}$ (cm³/g) | $V_{1 \mu m}$ (cm³/g) | Degree of adsorp-tion |
| --- | --- | --- | --- | --- | --- |
| Beads 6 | 1.2 | 175 | 0.70 | 0.34 | 85.4% |
| Beads 7 | 1.7 | 175 | 0.70 | 0.34 | 84.1% |
| Beads 8 | 2.4 | 175 | 0.70 | 0.34 | 76.3% |
| Beads 9 | 3.4 | 175 | 0.70 | 0.34 | 69.5% |
| Beads 10 | 3.15 | 335 | 0.26 | 0.15 | 60.7% |
| Beads 11 comparative | 4.5 | 335 | 0.26 | 0.15 | 53.6% |
| Beads 12 comparative | 4.70 | 335 | 0.26 | 0.15 | 52.2% |
| Beads 13 comparative | 5.5 | 335 | 0.26 | 0.15 | 46.4% |

It is found that the degree of adsorption of beads 11 to 13, exhibiting a diameter greater than 4 mm, does not exceed 60%, in contrast to beads 6 to 10, which conform to the characteristics of the beads according to the invention.

We claim:

1. Process for the adsorption of chelated organometallic compounds, comprising placing said compounds in contact with alumina-based beads produced by agglomeration of an alumina powder using a rotational technique and exhibiting a volume of pores having a diameter greater than 100 Å of at least 0.10 cm³/g, a volume of pores having a diameter greater than 1 μm of at least 0.05 cm³/g and a diameter of not more than 4 mm.

2. Process according to claim 1, characterized in that the specific surface of the beads is at least 100 m²/g.

3. Process according to claim 2, characterized in that the beads include at least one compound of an element chosen from the group including the alkali and alkaline-earth metals.

4. Process according to claim 3, characterized in that the content of the compound of the element chosen from the group of the alkali and alkaline-earth metals is between 15 mmol and 150 mmol per 100 g of alumina.

5. Process according to one of claims 1 to 4, characterized in that the beads are formed by agglomeration of an alumina powder using a coating pan or rotary drum.

6. Process according to claim 4 for the adsorption of chelated organometallic compounds based on metals chosen from those of the groups IVB, VB, VIB, VIIB, VIII, IB and IIB.

7. Process according to claim 6 for the adsorption of chelated organometallic compounds incorporating metals chosen from the group consisting of vanadium, titanium, zirconium and copper.

8. Process according to claim 7 for the adsorption of chelated organometallic compounds wherein the chelate is chosen from the group consisting of acetylacetone, 2-ethyl-1,3-hexanediol and di-2-ethylhexyl phosphate.

9. Process for removing metal residues from a mixture of polyolefins and metal residues produced by polymerization of olefins in the presence of a coordination catalyst system, comprising contacting the mixture of polyolefins and metal residues with organic compounds that form complexes with the metal residues therein to produce chelated organometallic compounds;

contacting the mixture of polyolefins and chelated organometallic compounds with alumina-based beads that adsorb the chelated organometallic compounds, wherein said alumina-based beads are produced by agglomeration of an alumina powder using a rotational technique, further wherein said alumina beads exhibit a volume of pores having a diameter greater than 100 Å of at least 0.10 cm³/g and a volume of pores having a diameter greater than 1 μm of at least 0.05 cm³/g, and further wherein said alumina-based beads have a diameter of not more than 4 mm; and separating the alumina-based beads including the adsorbed chelated organometallic compounds from the polyolefins.

10. Alumina-based beads including a chelated organometallic compound, produced by the process for removing metal residues from a mixture of polyolefins and metal residues resulting from the polymerization of olefins in the presence of a coordination catalyst system, said process comprising contacting the mixture of polyolefins and metal residues with organic compounds that form complexes with the metal residues therein to produce chelated organometallic compounds;

contacting the mixture of polyolefins and chelated organometallic compounds with alumina-based beads that adsorb the chelated organometallic compounds, wherein said alumina-based beads are produced by agglomeration of an alumina powder using a rotational technique, further wherein said alumina beads exhibit a volume of pores having a diameter greater than 100 Å of at least 0.10 cm³/g and a volume of pores having a diameter greater than 1 μm of at least 0.05 cm³/g, and further wherein said alumina-based beads have a diameter of not more than 4 mm; and separating the alumina-based beads including the adsorbed chelated organometallic compounds from the polyolefins.

* * * * *